(12) United States Patent
Moore et al.

(10) Patent No.: US 9,777,022 B2
(45) Date of Patent: Oct. 3, 2017

(54) PROCESS FOR THE PREPARATION OF MACROCYCLIC POLYAZACARBOXYLATE LIGANDS AND CHELATES

(71) Applicant: Mallinckrodt LLC, Hazelwood, MO (US)

(72) Inventors: Dennis A. Moore, Ferguson, MO (US); Raghavan Rajagopalan, St. Peters, MO (US)

(73) Assignee: GUERBET, Villepinte (FR)

( * ) Notice: Subject to any disclaimer, the term of this patent is extended or adjusted under 35 U.S.C. 154(b) by 0 days.

(21) Appl. No.: 15/061,649

(22) Filed: Mar. 4, 2016

(65) Prior Publication Data
US 2016/0185803 A1    Jun. 30, 2016

Related U.S. Application Data

(63) Continuation of application No. 14/433,308, filed as application No. PCT/US2013/062849 on Oct. 1, 2013, now Pat. No. 9,315,474.

(60) Provisional application No. 61/708,663, filed on Oct. 2, 2012.

(51) Int. Cl.
*C07F 5/00* (2006.01)
*C07D 257/02* (2006.01)
*C07D 295/15* (2006.01)

(52) U.S. Cl.
CPC ............ *C07F 5/003* (2013.01); *C07D 257/02* (2013.01); *C07D 295/15* (2013.01)

(58) Field of Classification Search
CPC ...... C07D 257/02; C07D 295/15; C07F 5/003
See application file for complete search history.

(56) References Cited

U.S. PATENT DOCUMENTS 5,744,616 A * 4/1998 Petrov .................. C07D 257/02
548/960

FOREIGN PATENT DOCUMENTS

| CZ | 297577 B6 | 1/2007 |
| WO | 96/28420 | 9/1996 |
| WO | 2014055504 A1 | 4/2014 |

OTHER PUBLICATIONS

Buoens, S., et al.; Twelve-ring Azacrowns with 2-Alkoxyethyl Side-Arms; Acta Chemica Scandinavica; 1986, pp. 278-282, vol. 40b.
Hansen, G.R., et al.; Unique Synthesis of 1,4,7,10-tetraazacyclododecan; Journal of Heterocyclic Chemistry; 1968; pp. 305, vol. 5, No. 1.
International Search Report and Written Opinion dated Nov. 26, 2013 from related International application No. PCT/US2013/062849, 9 pgs.

* cited by examiner

*Primary Examiner* — Erich A Leeser

(57) ABSTRACT

The present disclosure relates generally to a process for the synthesis of 1,4,7,10-tetraazacyclododecane ligands, chelates, and derivatives thereof. In particular, the present disclosure is directed to a process for the synthesis of 1,4,7,10-tetraaza-1,4,7,10-tetrakis(carboxymethyl)cyclododecane (DOTA) ligands, corresponding DOTA-metal chelates, and various derivatives thereof.

39 Claims, 3 Drawing Sheets

PROCESS FOR THE PREPARATION OF MACROCYCLIC POLYAZACARBOXYLATE LIGANDS AND CHELATES

CROSS REFERENCE TO RELATED APPLICATIONS

This application claims the priority of U.S. Ser. No. 14/433,308, filed Apr. 2, 2015, which claims priority to PCT Application PCT/US2013/062849, filed Oct. 1, 2013, which claims the benefit of US provisional application No. 61/708,663, filed Oct. 2, 2012, each of which is hereby incorporated by reference in its entirety.

FIELD OF THE DISCLOSURE

The present disclosure relates generally to a process for the synthesis of 1,4,7,10-tetraazacyclododecane ligands, chelates, and derivatives thereof. In particular, the present disclosure is directed to a process for the synthesis of 1,4,7,10-tetraaza-1,4,7,10-tetrakis(carboxymethyl)cyclododecane (DOTA) ligands, corresponding DOTA-metal chelates, and various derivatives thereof.

BACKGROUND

Polyaminocarboxylate ligands, and the chelates derived therefrom, have been widely used in medical diagnosis and therapy, such as for example in the field of Magnetic Resonance Imaging (MRI). Macrocyclic chelating agents, such as DOTA macrocyclic chelating agents, form particularly stable chelates with contrast-generating paramagnetic metal ions, and thus are suitable carriers for these metal ions. The gadolinium-DOTA chelate (Dotarem®) is one commercially available MRI agent. Radionuclide chelates, such as $^{177}$Lu-DOTA and $^{90}$Y-DOTA, conjugated to bioactive peptides have also been used as radioscintigraphic imaging and radiotherapeutic agents.

Lack of efficient and cost effective processes for the synthesis of polyazamacrocyclic ligands has been an obstacle toward widespread use of these types of ligands and associated chelates. Several synthetic routes for the preparation of DOTA are known. For instance, EP 232751 A (by Tweedle) and EP 292689 A (by Tweedle) disclose DOTA preparation by diamine:diamine or triamine:monoamine cyclic condensation.

A key intermediate in these procedures is 1,4,7,10-tetraazacyclododecane. Hansen, et al. (Hansen and Burg. *Journal of Heterocyclic Chemistry* 1968, 305) disclose that 1,4,7,10-tetra(benzyl)-1,4,7,10-tetraazacyclododecane can be produced by cylco-tetramerization of N-benzylaziridine according to the following reaction scheme:

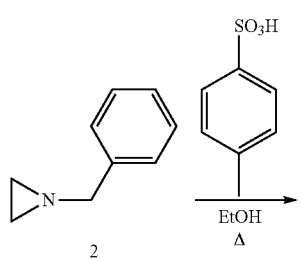

Notably, however, Hansen discloses that the cylco-tetramerization process shown above is unique to the N-benzylaziridine substrate, as only high molecular weight polymers, and not macrocycles, were generated when aziridine, N-methylaziridine, N-phenylaziridine and N-(β-hydroxymethyl) aziridine substrates were used.

Building upon Hansen, WO9628420A2[1] (WO '420 by Messerle) and U.S. Pat. No. 5,744,616 (U.S. '616, by Petrov) disclose a process for the preparation of DOTA and Dotarem® from N-benzylaziridine substrate according to the below reaction scheme, where WO '420 discloses isolation of each intermediate before proceeding to the subsequent process step and U.S. '616 discloses carrying each intermediate forward in solution.

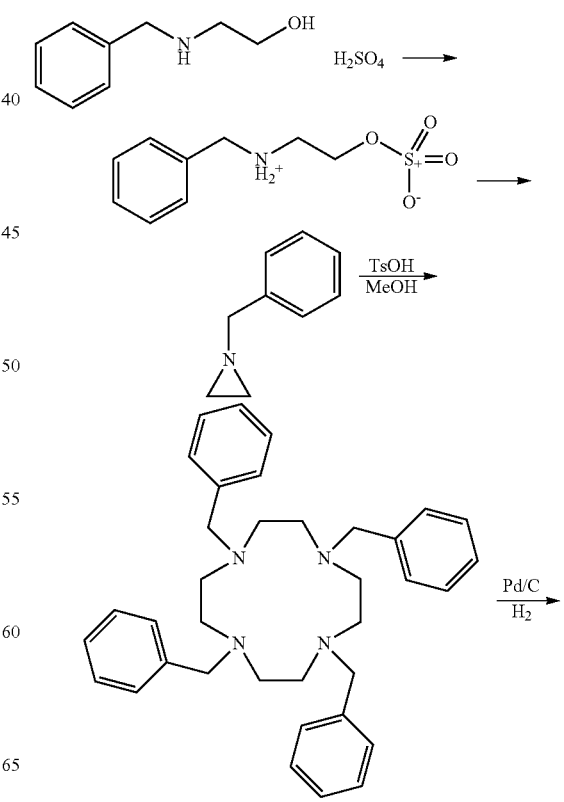

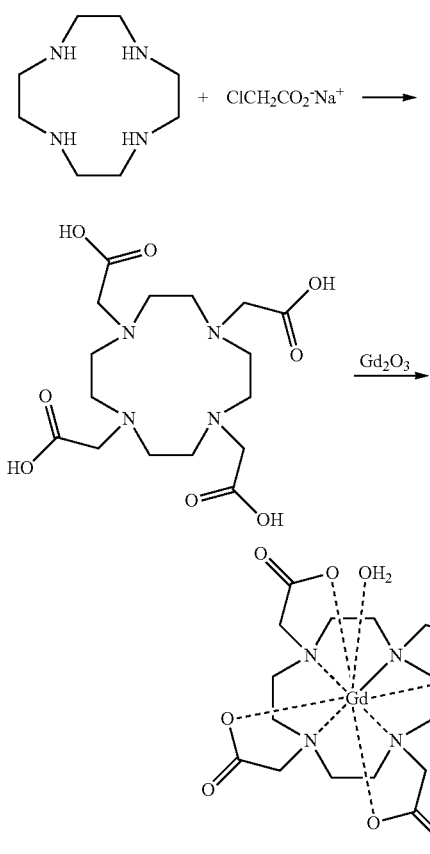

However, WO '420 and U.S. '616 disclose tetra-benzyl cyclized intermediate yields of about 28% and about 58%, respectively.

A need therefore exists for improved and simplified processes for the preparation of macrocyclic polyazacaboxylate ligands, and more specifically 1,4,7,10-tetraazacyclododecane derivatives, such as DOTA, DOTA-chelates, and derivatives thereof, in high yield and purity.

SUMMARY OF THE DISCLOSURE

Briefly, therefore, the present disclosure is directed to a process for the preparation of a macrocyclic tetramer compound of Formula (II). The process comprises forming a reaction mixture comprising a stoichiometric amount of (a) an aziridine of Formula (I), (b) a Brønsted acid, a Lewis acid, or a combination of a Brønsted acid and a Lewis acid, and (c) a solvent. The contents of the reaction mixture are reacted to form the compound of Formula (II) by cyclotetramerization of the aziridine of Formula (I), according to the following reaction:

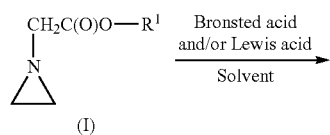

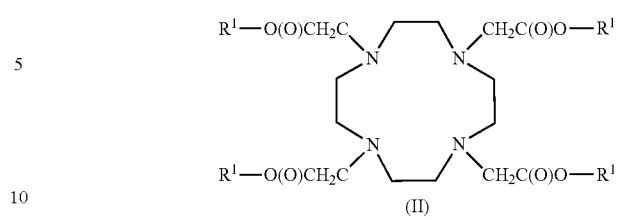

wherein each $R^1$ is independently selected from the group consisting of $C_{1-10}$ hydrocarbyl.

The present disclosure is also directed to a process for the preparation of 1,4,7,10-tetraaza-1,4,7,10-tetrakis(carboxymethyl)cyclododecane (DOTA). The process comprises forming a reaction mixture comprising (a) a stoichiometric amount of an aziridine of Formula (Ib), (b) a Brønsted acid, and (c) a solvent. The contents of the reaction mixture are reacted to form DOTA by cyclotetramerization of the aziridine of Formula (Ib), according to the following reaction:

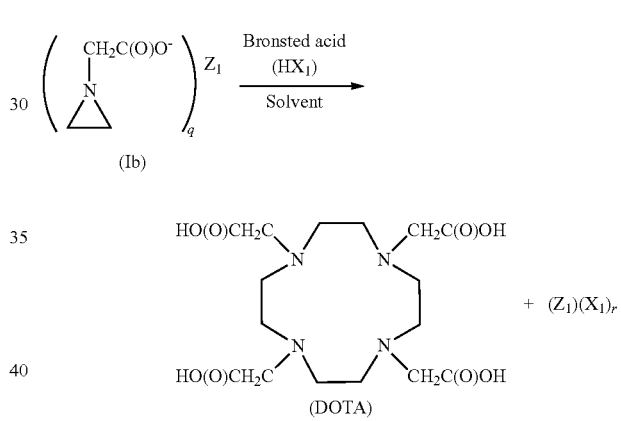

wherein $Z_1$ is an alkali metal having a +1 charge or an alkaline earth metal having a +2 charge and wherein q and r are 1 when $Z_1$ is an alkali metal and q and r are 2 when $Z_1$ is an alkaline earth metal.

The present disclosure is further directed to a process for the preparation of a macrocyclic tetramer compound of Formula (IIe). The process comprises forming a reaction mixture comprising (a) a stoichiometric amount of an aziridine of Formula (Ib), (b) a Lewis acid, and (c) a solvent. The contents of the reaction mixture are reacted to form a metal-1,4,7,10-tetraaza-1,4,7,10-tetrakis(carboxymethyl)cyclododecane (DOTA) chelate of Formula (IIe) by cyclotetramerization of the aziridine of Formula (Ib), according to the following reaction:

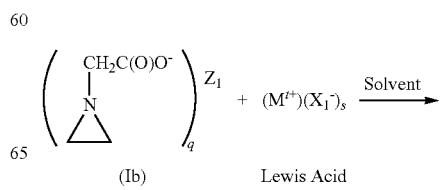

-continued

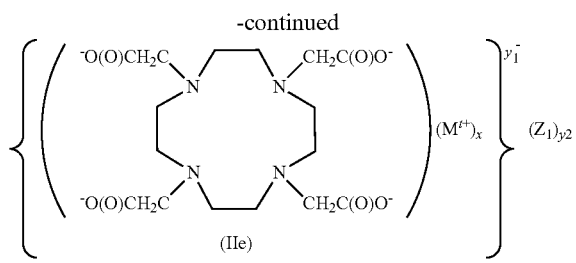

(IIe)

wherein $(M^{t+})(X_1^-)_s$ is a chelatable Lewis acid metal salt formed from a cation, M, and an anion, $X_1^-$, wherein t is 1, 2 or 3 and s is selected to achieve electrical neutrality, wherein $Z_1$ is hydrogen, an alkali metal having a +1 charge or an alkaline earth metal having a +2 charge, wherein q is 1 when $Z_1$ is an alkali metal and q is 2 when $Z_1$ is an alkaline earth metal, and wherein t is 3 and x is 1, or t is 2 and x is 1, or t is 2 and x is 2, or t is 1 and x is 1, or t is 1 and x is 2, or t is 1 and x is 3 or t is 1 and x is 4. As disclosed in the below table, when $Z_1$ has a +1 charge then $y_1=y_2=(4-(X*t))$, and when $Z_1$ has a +2 charge then $y_1=(4-(X*t))$ and $y_2=(y_1/2)$:

| t | X | $Z_1 = +1$ $y_1$ and $y_2$ | $Z_2 = +2$ $y_1$ | $y_2$ |
|---|---|---|---|---|
| 3 | 1 | 1 | 1 | ½ |
| 2 | 1 | 2 | 2 | 1 |
| 2 | 2 | 0 | 0 | 0 |
| 1 | 1 | 3 | 3 | 3/2 |
| 1 | 2 | 2 | 2 | 1 |
| 1 | 3 | 1 | 1 | ½ |
| 1 | 4 | 0 | 0 | 0 |

DETAILED DESCRIPTION

Figure 1:
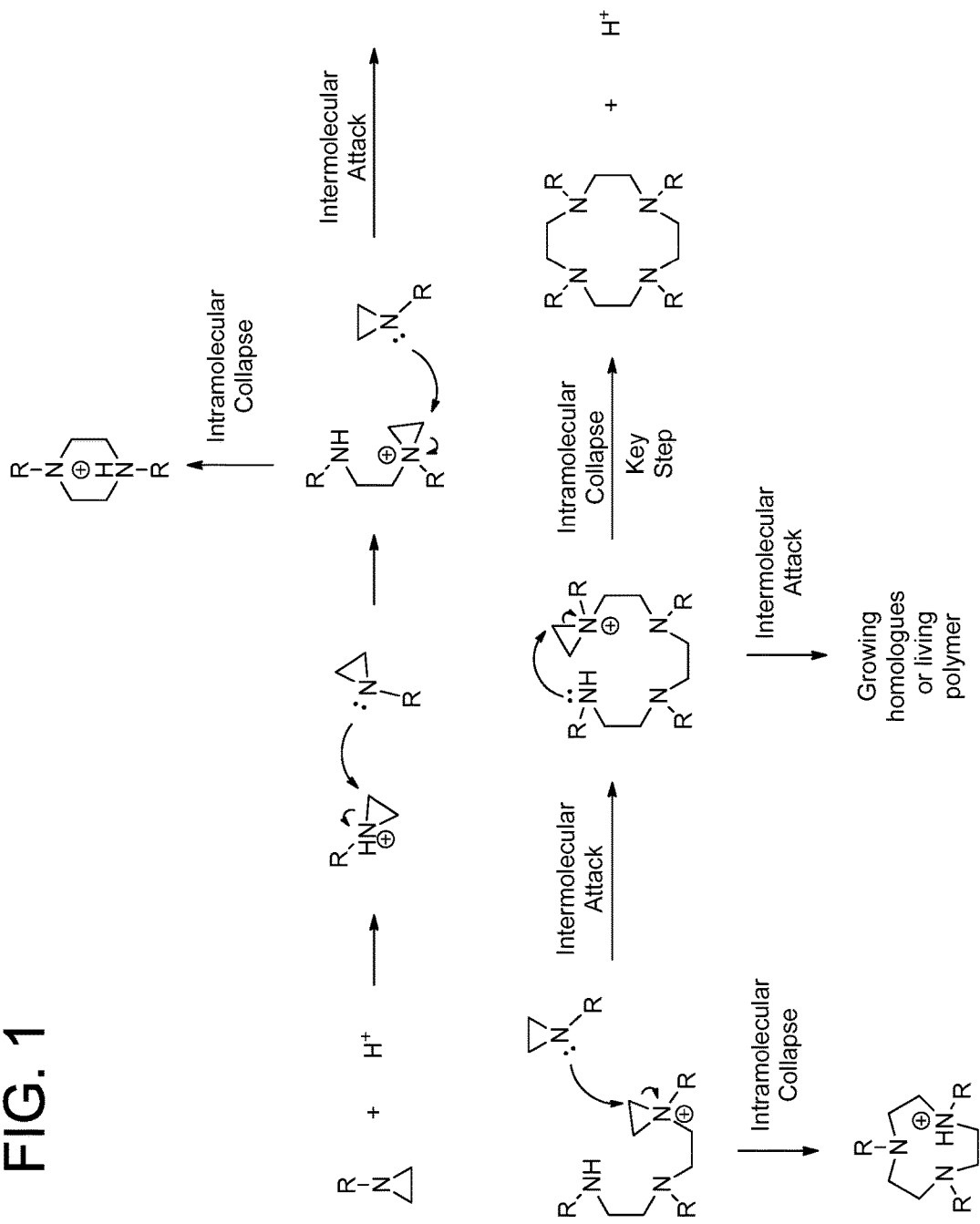
FIG. 1 is a proposed general mechanism for the reactivity of Lewis acid-activated aziridines.

The present disclosure generally provides for improved and simplified processes for the preparation of macrocyclic polyazacarboxylate ligands, and more particularly 1,4,7,10-tetraazacyclododecane ligands, as well as chelates and derivatives thereof. In one exemplary embodiment, the present disclosure provides for improved and simplified processes for the preparation of DOTA, DOTA-chelates, and derivatives thereof, in high yield and purity. In accordance with the present disclosure, it has been discovered that such ligands, particularly DOTA and DOTA-related derivatives, can be prepared from aziridine substrates in a simplified synthetic route that avoids the generation of tetra-benzyl cyclized intermediates. The various embodiments of the process of the present disclosure thereby eliminate the need for cleavage of arylmethyl groups from the ligand (e.g., DOTA or DOTA derivative), allowing for the simplified, more direct, synthesis and improved yield and purity thereof, as well as the chelates that may be formed therefrom.

In the various embodiments of the present disclosure, a substituted aziridine substrate is combined with a Brønsted acid, a Lewis acid, or a combination of a Brønsted acid and a Lewis acid, and a solvent to form a reaction mixture. A ligand (e.g., DOTA) or ligand-chelate (e.g., DOTA-chelate), or a derivative thereof, is then formed by the cyclotetramerization of aziridine.

In some aspects of the present disclosure a process for the preparation of a macrocyclic tetramer compound of Formula (II) is provided. The process comprises forming a reaction mixture comprising a stoichiometric amount of (a) an aziridine of Formula (I), (b) a Brønsted acid, a Lewis acid, or a combination of a Brønsted acid and a Lewis acid, and (c) a solvent. The contents of the reaction mixture are reacted to form the compound of Formula (II) by cyclotetramerization of the aziridine of Formula (I), according to the following Reaction Scheme 1:

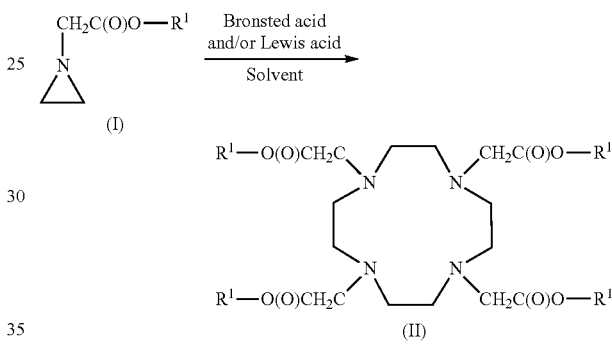

wherein each $R^1$ is independently selected from the group consisting of $C_{1-10}$ hydrocarbyl. In some embodiments, each $R^1$ is independently selected from methyl, ethyl, 2-propyl and benzyl. In some other embodiments, $R^1$ is methyl.

In some embodiments, the compounds of Formula (II) can be hydrolyzed or hydrogenated according to methods known the art to cleave $R^1$ and generate DOTA.

In some other Reaction Scheme 1 embodiments, the acid is a Brønsted acid and the reaction mixture further comprises an alkali metal salt, $(Z_2^{m+})(X_2)_p$, wherein Formula (IIa) is formed by cyclotetramerization of the aziridine of Formula (I) according the following Reaction Scheme 2:

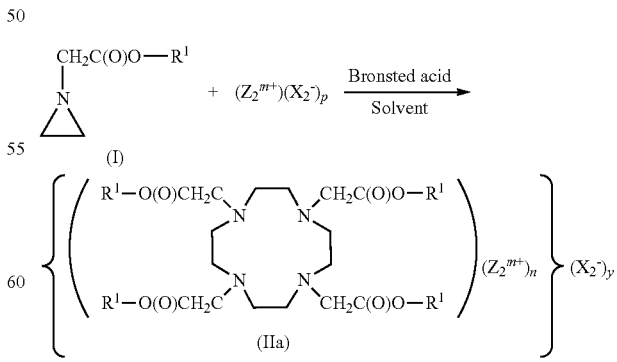

In any of these embodiments, $Z_2^{m+}$ is a counterion selected from the group consisting of a hydrogen ion, a tertiary ammonium ion, an alkali metal ion, and an alkaline earth metal, wherein m+ is 1 or 2; $X_2^-$ is selected from the group consisting of a halide, p-toluenesulfonate and trifluoroacetate; p is the number of $X_2^-$ needed to maintain electrical neutrality with $Z_2^{m+}$ and is selected from 1 and 2; n is an integer selected from 0 to 4; and y is the number of $X_2^-$ needed to maintain electrical neutrality of formula (IIa). In some embodiments, $Z_2$ is sodium or potassium and $X_2^-$ is chloride or bromide.

In yet other Reaction Scheme 1 embodiments, the acid is a Brønsted acid, the process further comprising contacting Formula (II) with an alkali metal salt, $(Z_2^{m+})(X_2^-)_p$, to form Formula (IIa):

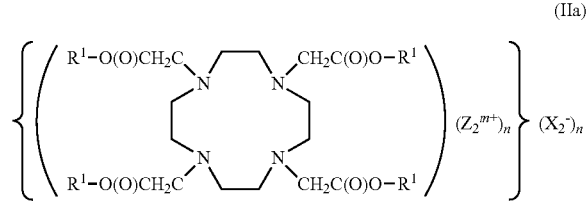

(IIa)

In any of these embodiments, $Z_2^{m+}$ is a counterion selected from the group consisting of a hydrogen ion, a tertiary ammonium ion, an alkali metal ion, and an alkaline earth metal, wherein m+ is 1 or 2; $X_2^-$ is selected from the group consisting of a halide, p-toluenesulfonate and trifluoroacetate; p is the number of $X_2^-$ needed to maintain electrical neutrality with $Z_2^{m+}$ and is selected from 1 and 2; n is an integer selected from 0 to 4; and y is the number of $X_2^-$ needed to maintain electrical neutrality of formula (IIa). In some embodiments, $Z_2$ is sodium or potassium and $X_2$ is chloride or bromide.

In one Reaction Scheme 1 embodiment, gadoteric acid is prepared according to the following reaction scheme:

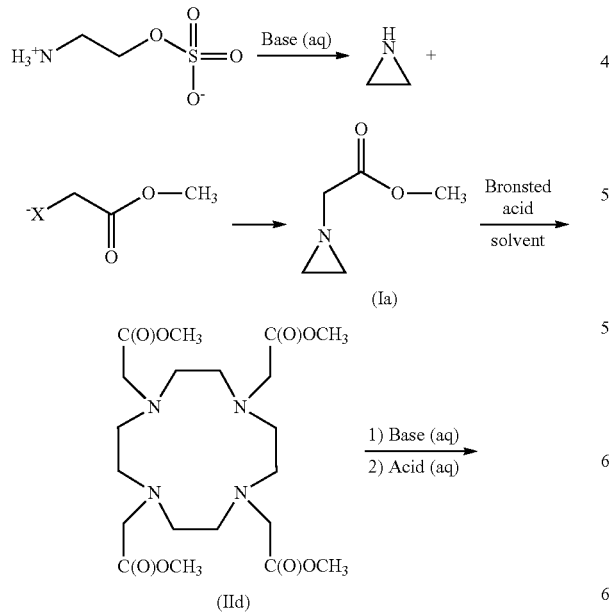

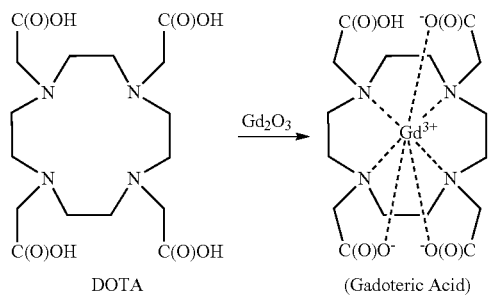

wherein the base is a metallic base such as, for instance, sodium hydroxide or potassium hydroxide; $X^-$ is an anion such as a halide; the acid is a mineral acid such as, for instance, HCl; and the Brønsted acid and solvent are as disclosed below. In one embodiment, the base is NaOH, the acid is HCl, the solvent is methanol and the Brønsted acid is p-toluenesulfonic acid.

In some other aspects of the present disclosure, a process for the preparation of DOTA is provided. The process comprises forming a reaction mixture comprising (a) a stoichiometric amount of an aziridine of Formula (Ib), (b) a Brønsted acid, and (c) a solvent. The contents of the reaction mixture are reacted to form DOTA by cyclotetramerization of the aziridine of Formula (Ib), according to the following Reaction Scheme 3:

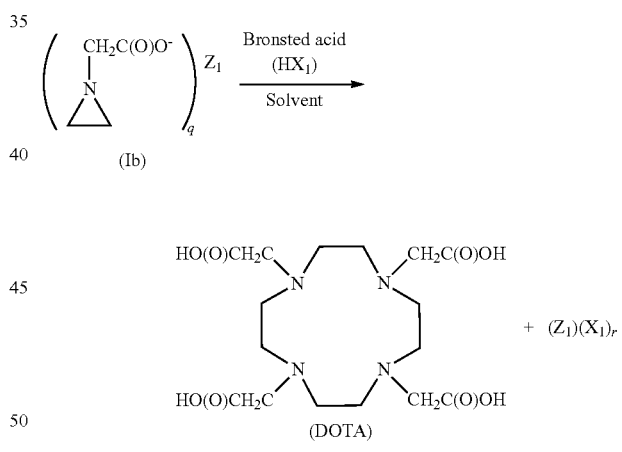

wherein $Z_1$ is an alkali metal having a +1 charge or an alkaline earth metal having a +2 charge and wherein q and r are 1 when $Z_1$ is an alkali metal and q and r are 2 when $Z_1$ is an alkaline earth metal. In some embodiments, $Z_1$ is $Na^+$, $K^+$, $Ca^{2+}$ or $Mg^{2+}$ and $X_1$ is $Br^-$, $Cl^-$ or $OSO_3^{2-}$. In some embodiments, the solvent comprises water, and in other embodiments, the solvent consists essentially of water.

In some embodiments, DOTA can be treated with a metal cation, $M^{n+}$, wherein n+ is 2 or 3, provided from a metal ion source selected from the group consisting of metal oxides, metal carbonates, and weak chelates to form a metal-DOTA chelate of Formula (IIb) or Formula (IIc):

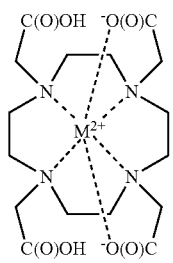

(IIb)

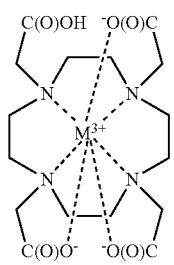

(IIc)

wherein the metal cation is selected from the group consisting of Gd, Eu, Tb, Dy, Sm, Lu, La, In, Ga, Re, Ru, Fe, Cu, Zn, Ni, Co, Cr, V, Ti Sc, Zr, Nb, Mo, Rh, Pd, Ag, Cd, Sn, Hf, Ta, W, Os, Ir, Pt, Au and Y, and wherein $M^{2+}$ coordination can occur with any two of the carboxyl moieties. In some embodiments, the metal ion source is an oxide, carbonate, weak chelate or other metal salt of Gd, Eu, Tb, Dy, Sm, Lu, La, In, Ga, Re, Ru, Fe, Cu, Zn, Ni, Co, Cr, V, Ti Sc, Zr, Nb, Mo, Rh, Pd, Ag, Cd, Sn, Hf, Ta, W, Os, Ir, Pt, Au or Y ions. In some other embodiments, the weak chelate is an acetylacetonate chelate. In some embodiments, the metal ion source is a chelate of acetylacetonate or $Gd_2O_3$ and compound Formula (IIc) is gadoteric acid. Metal chelation of DOTA ligands can be accomplished by the methods well known in the art, such as described by Hancock, R., et al., *Ligand Design for Selective Complexation of Metal Ions in Aqueous Solution*, Chem. Rev. 1989, 89, 1875-1914; or alternatively as described in U.S. Pat. No. 4,822,594 (by Gibby) and United States Patent Application Publication No. US 2009/0036674 A1 (by Moore), which are incorporated in their entirety herein by reference, for all relevant and consistent purposes In some other aspects of the present disclosure, a process for the preparation of a macrocyclic tetramer compound of Formula (IIe) is provided. The process comprises forming a reaction mixture comprising (a) a stoichiometric amount of an aziridine of Formula (Ib), (b) a Lewis acid, and (c) a solvent. The reaction mixture is reacted to form a metal-DOTA chelate of Formula (IIe) by cyclotetramerization of the aziridine of Formula (Ib), according to the following Reaction Scheme 4:

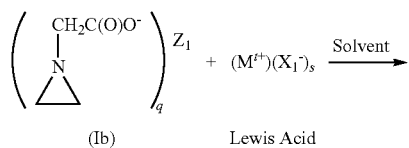

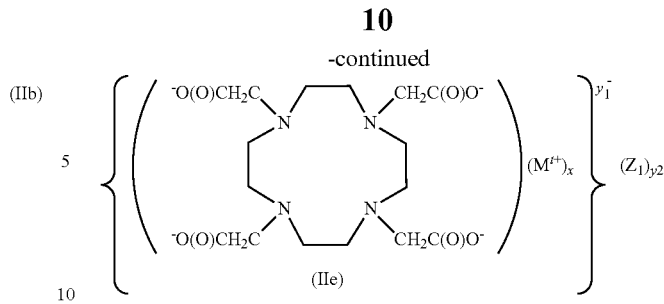

(IIe)

wherein $(M^{t+})(X_1^-)_s$ is a chelatable Lewis acid metal salt formed from a cation, M, and an anion, $X_1^-$, wherein t is 1, 2 or 3 and s is selected to achieve electrical neutrality, wherein $Z_1$ is hydrogen, an alkali metal having a +1 charge or an alkaline earth metal having a +2 charge, wherein q is 1 when $Z_1$ is an alkali metal and q is 2 when $Z_1$ is an alkaline earth metal, and wherein t is 3 and x is 1, or t is 2 and x is 1, or t is 2 and x is 2, or t is 1 and x is 1, or t is 1 and x is 2, or t is 1 and x is 3 or t is 1 and x is 4. As disclosed in Table A below, when $Z_1$ has a +1 charge then $y_1=y_2=(4-(X*t))$, and when $Z_1$ has a +2 charge then $y_1=(4-(X*t))$ and $y_2=(y_1/2)$:

TABLE A

| t | X | $Z_1 = +1$ $y_1$ and $y_2$ | $Z_2 = +2$ $y_1$ | $y_2$ |
|---|---|---|---|---|
| 3 | 1 | 1 | 1 | ½ |
| 2 | 1 | 2 | 2 | 1 |
| 2 | 2 | 0 | 0 | 0 |
| 1 | 1 | 3 | 3 | 3/2 |
| 1 | 2 | 2 | 2 | 1 |
| 1 | 3 | 1 | 1 | ½ |
| 1 | 4 | 0 | 0 | 0 |

In some embodiments, the solvent comprises water, and in other embodiments, the solvent consists essentially of water.

In some Reaction Scheme 4 embodiments, Formula (IIe) is of Formula (IIf):

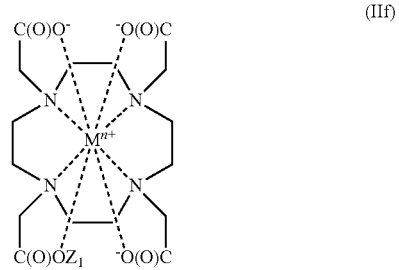

(IIf)

wherein n is 3 and $Z_1$ is hydrogen or an alkali metal having a +1 charge. In some further embodiments, Formula (IIf) is gadoteric acid wherein $M^{n+}$ is $Gd^{3+}$ and $Z_1$ is hydrogen. In one particular embodiment, Formula (IIf) is gadoteric acid, formed for example by the cyclotetramerization of sodium 2-methylaziridinylacetate by gadolinium chloride at a pH of about −1 to about 2.

Without being bound to any particular theory, the cyclotetramerization reaction appears to be primarily driven by two factors: (i) steric effects resulting from the bulk of the R-group on the aziridine nitrogen; and, (ii) the basicity of the aziridine nitrogen. It is generally believed that activated aziridines, bearing electronegative functionalities such as carbonyl (amide) or sulfonyl (sulfonamide) groups, stabilize the resultant anion formed by nucleophilic attack on the aziridine ring. Unactivated aziridines bearing alkyl substituents typically require assistance by Lewis or Brønsted acids for reactivity. It is further believed that treatment of protio- or alkyl-substituted aziridine with such acids results in the formation of a cationic aziridinium, which is susceptible towards attacks by nucleophiles, resulting in cyclotetramerization. However, cationic aziridinium is also susceptible to attack by unactivated aziridines, which may result in polymer formation. Both types of reactions are generally well-known in the art. (See, e.g., Pulipaka, *Journal of Organic Chemistry* 2008, 73, 1462; Watson, *Accounts of Chemical Research* 2006, 36, 194; Hashimoto, *Journal of Macromolecular Science Chemistry* 1984, A21 (6-7), 875; and Stephens, *Journal of Chemical and Engineering Data* 1969, 14, 114.) The observation of piperazine and polymer formation from 1-ethylaziridine and simple Brønsted acids has also been reported. (See, e.g., Dick, *Journal of Organic Chemistry* 1970, 3950.) The general mechanism for the reactivity of Lewis acid-activated aziridines has been suggested by Dick, and is outlined in FIG. 1 herein. Under this theory, it is believed that protonation of the aziridinyl nitrogen by the acid activates the ring towards nucleophilic attack by non-protonated aziridine. The subsequent aziridinium intermediate can then proceed down two paths: (i) intramolecular collapse, to make a cyclized product; or, (ii) intermolecular attack, to grow the chain. It is believed that the macrocyclic tetramer compounds of the present disclosure are predominantly formed by intramolecular collapse. It is further believed that additional tetramer could additionally be formed by the combination of two diamino moieties, thereby forming the tetramer in a more direct fashion according to the following mechanism:

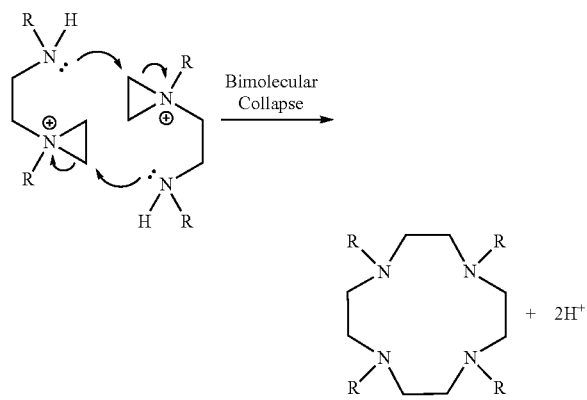

Brønsted Acids and Lewis Acids

Suitable Brønsted and Lewis acids for the practice of the present disclosure may be selected from acids generally known in the art.

Brønsted acids may be selected from p-toluenesulfonic acid, methane sulfonic acid, triflic acid, sulfuric acid, hydrochloric acid, hydroiodic acid, hydrobromic acid, hydrofluoric acid, phosphoric acid, perchloric acid, trifluoroacetic acid, triethylammonium chloride, triethylammonium bromide, triethylammonium acetate, triethylammonium formate, tris(2-hydroxyethyl)ammonium chloride, tris(2-hydroxyethyl)ammonium bromide, tris(2-hydroxyethyl)ammonium acetate, tris(2-hydroxyethyl)ammonium formate, 4,7,13,16,21,24-hexaoxa-1,10-diazabicyclo [8.8.8] hexacosan-1-ium chloride, bromide, tris(2-hydroxyethyl) ammonium acetate, 4,7,13,16,21,24-hexaoxa-1,10-diazabicyclo[8.8.8]hexacosan-1-ium formate, bis(isopropyl) ethylammonium chloride, bis(isopropyl)ethylammonium bromide, bis(isopropyl)ethylammonium acetate, bis(isopropyl)ethylammonium formate, tris(carboxymethyl)ammonium chloride, tris(carboxymethyl)ammonium bromide, tris (carboxymethyl)ammonium acetate, tris(carboxymethyl) ammonium formate, 2-(bis(carboxymethyl)amino)-N,N-bis (carboxymethyl)ethanaminium chloride, 2-(bis (carboxymethyl)amino)-N,N-bis(carboxymethyl) ethanaminium bromide, 2-bis(carboxymethyl)amino)-N,N-bis(carboxymethyl)ethanaminium acetate, bis 2-bis (carboxymethyl)amino)-N,N-bis(carboxymethyl) ethanaminium formate, 2-bis(carboxymethyl)amino)-N-(2-(bis(carboxymethyl)amino)ethyl)-N-(carboxymethyl) ethanaminium, 2-(bis(carboxymethyl)amino)-N-(2-(bis (carboxymethyl)amino)ethyl)-N-(carboxymethyl) ethanaminium bromide, 2-(bis(carboxymethyl)amino)-N-(2-(bis(carboxymethyl)amino)ethyl)-N-(carboxymethyl) ethanaminium acetate, 2-(bis(carboxymethyl)amino)-N-(2-(bis(carboxymethyl)amino)ethyl)-N-(carboxymethyl) ethanaminium formate, formic acid, acetic acid, succinic acid, benzoic acid, lactic acid, citric acid, oxalic acid, nitriloacetic acid, ethylenediaminetetraacetic acid, diethylenetriaminepentacetic acid and combinations thereof. In some embodiments, the Brønsted acid is selected from sulfuric acid, hydrochloric acid, trifluoroacetic acid, p-toluene sulfonic acid, hydroiodic acid, hydrobromic acid, hydrofluoric acid, phosphoric acid and perchloric acid, methane sulfonic acid and triflic acid, and combinations thereof. In some other embodiments, the Brønsted acid is selected from hydrochloric acid, sulfuric acid, trifluoroacetic acid and p-toluene sulfonic acid, and combinations thereof.

In the various embodiments of the present disclosure, the amount of the Brønsted acid, expressed as the ratio of equivalents of the acid to equivalents of aziridine compound, is from about 0.01:1 to about 0.5:1, from about 0.03:1 to about 0.1:1, or from about 0.04:1 to about 0.08:1.

Lewis acids are generally a chelatable Lewis acid metal salt formed from a metal cation, M, and a counterion, wherein M is selected from an alkali metal, an alkaline earth metal, a rare earth metal, a transition metal and a lanthanide metal. Examples of such acids include, but are not limited to, boron tribromide, boron trichloride, boron trifluoride, boron trifluoride etherate, gadolinium tribromide, gadolinium trichloride, gadolinium trifluoride, gadolinium acetate, gadolinium formate, cupric bromide, cupric chloride, cupric fluoride, nickel bromide, nickel chloride, nickel fluoride aluminum bromide, aluminum chloride, aluminum fluoride, ferric bromide, ferric chloride, ferric fluoride, sodium bromide, potassium bromide, potassium chloride, potassium fluoride, sodium chloride, sodium fluoride, tin(IV) chloride, and combinations thereof. In some embodiments, the acid is selected from sodium bromide, sodium chloride, sodium fluoride, sodium bromide, potassium bromide, potassium chloride, potassium fluoride, potassium bromide, gadolinium tribromide, gadolinium trichloride, gadolinium trifluoride, gadolinium acetate, gadolinium formate, and combinations thereof. In some other embodiments, the Lewis acid is selected from boron tribromide, boron trichloride, aluminum chloride, ferric chloride, tin(IV) chloride, and combinations thereof. In some embodiments the Lewis acid is suitably selected from gadolinium acetate and gadolinium chloride, or a combination thereof. In some other embodiments, is suitably selected from sodium bromide, sodium chloride, sodium iodide and combinations thereof.

In the various embodiments of the present disclosure, the amount of the Lewis acid, expressed as the ratio of equivalents of the acid to equivalents of aziridine compound, is from about 0.05:1 to about 1.5:1, from about 0.05:1 to about 1.2:1, or from about 0.5:1 to about 1.2:1. In some embodiments, the ratio of Lewis acid to aziridine is from about 0.05:1 to about 0.5:1 or from about 0.1:1 to about 0.5:1. In some other embodiments, the ratio of Lewis acid to aziridine is from about 1.0:1 to about 1.5:1 or from about 1.0:1 to about 1.2:1.

In other alternative embodiments, the acid comprises, at least one Brønsted acid selected from the species disclosed above and at least one Lewis acid selected from the species disclosed above. In some embodiments, the Brønsted acid is selected from sulfuric acid, hydrochloric acid, trifluoroacetic acid, p-toluene sulfonic acid, hydroiodic acid, hydrobromic acid, hydrofluoric acid, phosphoric acid, perchloric acid, methane sulfonic acid and triflic acid, and combinations thereof, and the Lewis acid is selected from sodium bromide, sodium chloride, sodium fluoride, sodium bromide, potassium bromide, potassium chloride, potassium fluoride, potassium bromide, gadolinium bromide, gadolinium trichloride, gadolinium trifluoride, gadolinium acetate, gadolinium formate, and combinations thereof. In some other embodiments, the Brønsted acid is selected from hydrochloric acid, sulfuric acid, trifluoroacetic acid and p-toluene sulfonic acid, and combinations thereof, and the Lewis acid is selected from boron tribromide, boron trichloride, aluminum chloride, ferric chloride and tin(IV) chloride, and combinations thereof. In some other embodiments, the Brønsted acid is selected from hydrochloric acid, sulfuric acid, trifluoroacetic acid, p-toluene sulfonic acid, and combinations thereof, and the Lewis acid is selected from sodium, potassium, gadolinium salts, and combinations thereof. In yet other embodiments, the Brønsted acid is p-toluene sulfonic acid and the Lewis acid is selected from sodium bromide and gadolinium acetate. In still other embodiments, the Brønsted acid is suitably selected from trifluoroacetic acid, p-toluene sulfonic acid, sulfuric acid, hydrochloric acid, and combinations thereof, and the Lewis acid is suitably selected from gadolinium acetate and gadolinium chloride, or a combination thereof. In yet other embodiments, the Brønsted acid is suitably selected from trifluoroacetic acid, p-toluene sulfonic acid, sulfuric acid, hydrochloric acid, and combinations thereof, and the Lewis acid is suitably selected from sodium bromide, sodium chloride, sodium iodide and combinations thereof.

In the various embodiments of the present disclosure for the combination of at least one Brønsted acid and at least one Lewis acid, the ratio of the Brønsted acid(s) (equivalent basis) to aziridine (molar basis) is from about 0.01:1 to about 0.5:1, from about 0.03:1 to about 0.1:1, or from about 0.04:1 to about 0.08:1 and the ratio of the Lewis acid(s) to the aziridine is from about 0.05:1 to about 1.5:1, from about 0.05:1 to about 1.2:1, or from about 0.5:1 to about 1.2:1. In some of these embodiments, the ratio of Lewis acid to aziridine is from about 0.05:1 to about 0.5:1. In some other embodiments, the amount of the Lewis acid in a ratio to aziridine of from about 1.0:1 to about 1.2:1.

Aziridine Substrates

Aziridine substrate compounds within the scope of the present disclosure may be prepared according to methods known to those skilled in the art, such as disclosed for example by U.S. Pat. No. 6,288,224 B1. For instance, aziridine Formula (I) may be prepared according to the reaction scheme below:

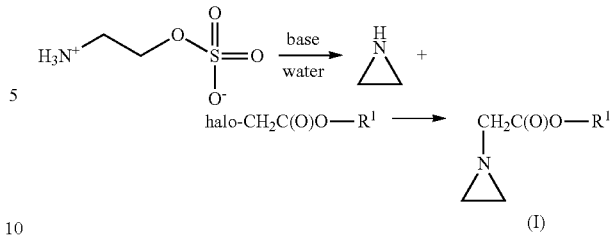

(I)

wherein $R^1$ is as defined above.

In one embodiment, aziridine of Formula (Ib) is prepared according to the reaction scheme below:

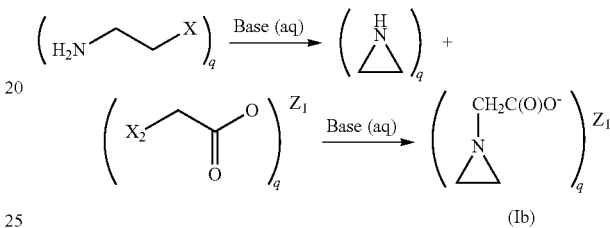

(Ib)

wherein X is a leaving group, $X_2$ is a halide, $Z_1$ is an alkali metal having a +1 charge or an alkaline earth metal having a +2 charge, q is 1 when $Z_1$ has a +1 charge, and q is 2 when $Z_1$ has a +2 charge. In some other embodiments, X is Cl, Br or $OSO_3H$, the base is NaOH or KOH and $Z_1$ is $Na^+$, $K^+$, $Ca^{2+}$ or $Mg^{2+}$.

Solvent

Generally speaking, the solvent may be selected from those generally known in the art for use in such a reaction. In particular, however, the solvent is suitably a polar aprotic solvent, a polar protic solvent, or a combination thereof. Polar aprotic solvents include, for example, chloroform, dichloromethane, tetrahydrofuran, ethyl acetate, acetone, dimethylformamide, dimethylacetamide, acetonitrile, 1,4-dioxane, glyme, diglyme, dimethyl sulfoxide, propylene carbonate, and combinations thereof. Polar protic solvents include, for example, methanol, ethanol, n-propanol, i-propanol, n-butanol, i-butanol, t-butanol, ethylene glycol, formic acid, water, acetic acid, and combinations thereof. In some other particular embodiments, the solvent is acetonitrile, dimethylacetamide, dimethylformamide, methanol or ethanol, or a combination thereof. In some particular embodiments, the solvent is an alcohol (or a mixture containing an alcohol) of the formula R'OH, wherein R' corresponds to the aziridine $R^1$ moiety, such as wherein both R' and $R^1$ are methyl. In yet other embodiments, the solvent comprises water or consists essentially of water. As used herein, a solvent "consisting essentially of water" does not exclude the presence of other solvents in amounts that do not materially affect the characteristics of the present disclosure.

Reaction Conditions

In any of the various embodiments of the present disclosure, the reaction temperature may be from about –20° C. to about 150° C., from about 0° C. to about 100° C., from about 10° C. to about 50° C., or from about 20° C. to about 30° C. In this regard it is to be noted, however, that preferred reaction temperatures may vary, for example, as a function of the solvent system, acid or acid system, the equivalent ratio thereof to aziridine, and/or the aziridine concentration in the reaction system.

In any of the various embodiments of the present disclosure, the concentration of the aziridine substrate compound in the reaction mixture comprising the solvent may typically be from about 0.05 to about 1.0 moles per liter, from about 0.1 to about 0.5 moles per liter, or from about 0.1 to about 0.3 moles per liter.

Yield/Purity

Any of the various reaction products of the present disclosure can be isolated and optionally purified by means known to those skilled in the art. In some embodiments, any of Formulae (II) to (III), DOTA or gadoteric acid may be isolated by crystallization or precipitation from a solvent, such as by induction of super saturation therein by, for instance, evaporation, temperature reduction, pH adjustment and/or the addition of co-solvents in which the reaction product is no more than sparingly soluble. Suitable purification techniques include, for instance, precipitation, crystallization, ultrafiltration and nanofiltration. In some further embodiments, the reaction products may be isolated and/or purified by crystallization from an aqueous solvent at a pH of from about 1 to about 4. When the reaction product is gadoteric acid, the crystallization pH from aqueous solvent is preferably from about 2 to about 4. In some particular embodiments, gadoteric acid purification may be achieved by one of the following non-limiting examples: (i) adjustment to a pH of about 0.5 to about 3, followed by solvent removal, crystallization or precipitation; (ii) preparative chromatography, such as liquid chromatography, ion exchange chromatography or size-exclusion chromatograph, with or without pH adjustment; or, (iii) nanofiltration at essentially neutral pH by meglumine addition. In some other embodiments, DOTA purification can be achieved by nanofiltration as the sodium salt thereof.

Notably, it has been discovered that the process of the present disclosure provides for high yield and/or purity of the desired macrocyclic tetramer compounds. The purity of compounds of Formulae (II)-(IIf), DOTA and gadoteric acid obtained from the process of the present disclosure is typically at least about 50%, at least about 60%, at least about 70%, at least about 80%, at least about 90%, or more, as measured by methods known to those skilled in the art such as, for example, MS chromatogram or evaporative light scattering (ELSD). Additionally, the molar yield of compounds of Formulae (II)-(IIf), DOTA and gadoteric acid obtained from the process of the present disclosure is typically at least about 40%, at least about 50%, at least about 60%, at least about 70%, at least about 80%, at least about 90%, or more, based on moles of aziridine used therein.

It is to be noted that the selection of combinations of (i) Brønsted acid and/or Lewis acid, (ii) solvent, (iii) equivalent ratios of Brønsted acids and/or Lewis acids to aziridine, (iv) aziridine species and concentration, and/or (v) reaction conditions (e.g., reaction temperature, reaction time, etc.,) within the scope of the present disclosure can affect macrocyclic polyazacarboxylate yield from aziridine. Without being bound to any particular embodiment and based on experimental evidence to date, Table B below depicts some observed macrocyclic polyazacarboxylate yields from aziridine Formula (I), wherein $R^1$ is methyl, for various combinations of a Brønsted acid and polar protic solvent or polar aprotic solvent (wherein DMAc refers to dimethylacetamide, DMF refers to dimethylformamide, MeOH refers to methyl alcohol, ACN refers to acetonitrile, TsOH refers to p-toluene sulfonic acid, and TFA refers to trifluoroacetic acid).

TABLE B

| Solvent/Acid | TFA | TsOH*H$_2$O | H$_2$SO$_4$ | HCl |
|---|---|---|---|---|
| DMAc | 68% yield | 92% yield | 81% yield | 8% yield |
| DMF | 68% yield | 74% yield | 66% yield | 8% yield |
| MeOH | 62% yield | 57% yield | 48% yield | 49% yield |
| ACN | 64% yield | 66% yield | 59% yield | 63% yield |

In this regard it is to be further noted that, in view of the present disclosure, selection and optimization of the various combinations of Brønsted acids and/or Lewis acids, solvents, equivalent ratios of Brønsted acids and/or Lewis acids to aziridine, aziridine concentration, and/or reaction conditions for the purpose of achieving significant and commercially acceptable macrocyclic polyazacarboxylate yield and purity, is within the purview of one skilled in the art.

Definitions

The term "hydrocarbyl" as used herein describes an organic compound or radical consisting exclusively of the elements carbon and hydrogen. This moiety includes alkyl, alkenyl, alkynyl, and aryl moieties. This moiety also includes alkyl, alkenyl, alkynyl, unsaturated or partially saturated cyclic moieties, aryl and aryl moieties substituted with other aliphatic or cyclic hydrocarbon groups, such as alkaryl, alkenaryl and alkynaryl. Unless otherwise indicated, this moiety preferably contains 1 to 10 carbon atoms.

The term "aryl" or as used herein alone or as part of another group denote optionally substituted homocyclic aromatic groups, preferably monocyclic or bicyclic groups containing from 4 to 10 carbons, from 4 to 8 carbons or from 5 to 8 carbons in the ring portion, such as phenyl, biphenyl, naphthyl, substituted phenyl (e.g., alkylphenyl), substituted biphenyl or substituted naphthyl. Phenyl and alkylphenyl (e.g., benzyl) are the more preferred aryl.

The term "Lewis acid" is defined as a molecule or ion (electrophile) that can combine with another molecule or ion by forming a dative bond by accepting one or more electron pairs from that second molecule or ion.

The term "Brønsted" acid is defined as a molecule or ion that is able to lose, or "donate," a hydrogen cation (H$^+$).

The term "halo" or "halogen" as used herein alone or a part of another group refers to chlorine, bromine, fluorine, and iodine.

The term "chelate" as used herein refers to a macrocycle of the disclosure complexed or coordinated with a metal.

The term "derivative" refers to a macrocylcic polyazacarboxylate compound or ligand (e.g., DOTA) having at least one chemical modification thereto, either on the macrocyclic polyazacaboxylate ring itself or at a functional group thereon.

EXAMPLES

The following non-limiting examples are provided to further illustrate the present disclosure.

Example 1: Preparation of tetramethyl 2,2',2",2"'-(1,4,7,10-tetraazacyclododecane-1,4,7,10-tetrayl)tetraacetate (DOTA-tetra(methyl ester)) (i.e., a Compound of Formula (II), Wherein —$R^1$=—$CH_3$)

Three solutions were prepared in vials as indicated in Table 1 below, wherein the methyl 2-aziridinylacetate solution contained (20 μL, 184 mmol) methyl 2-aziridinylacetate in acetonitrile (ACN 1.8 mL) was treated with p-toluenesulfonic acid (1.48 mg, 9.21 mmol).

TABLE 1

| Vial | 1 | 2 | 3 |
|---|---|---|---|
| uL of methyl 2-aziridinylacetate solution | 20 | 20 | 20 |
| Millimoles of methyl 2-aziridinylacetate | 184 | 184 | 184 |
| Millimoles of p-toluenesulfonic acid | 9.21 | 18.4 | 36.8 |
| Mole fraction p-toluenesulfonic acid | 0.05 | 0.1 | 0.2 |
| uL of 10 mg/mL p-toluenesulfonic acid solution | 148 | 295 | 590 |

Figure 2:
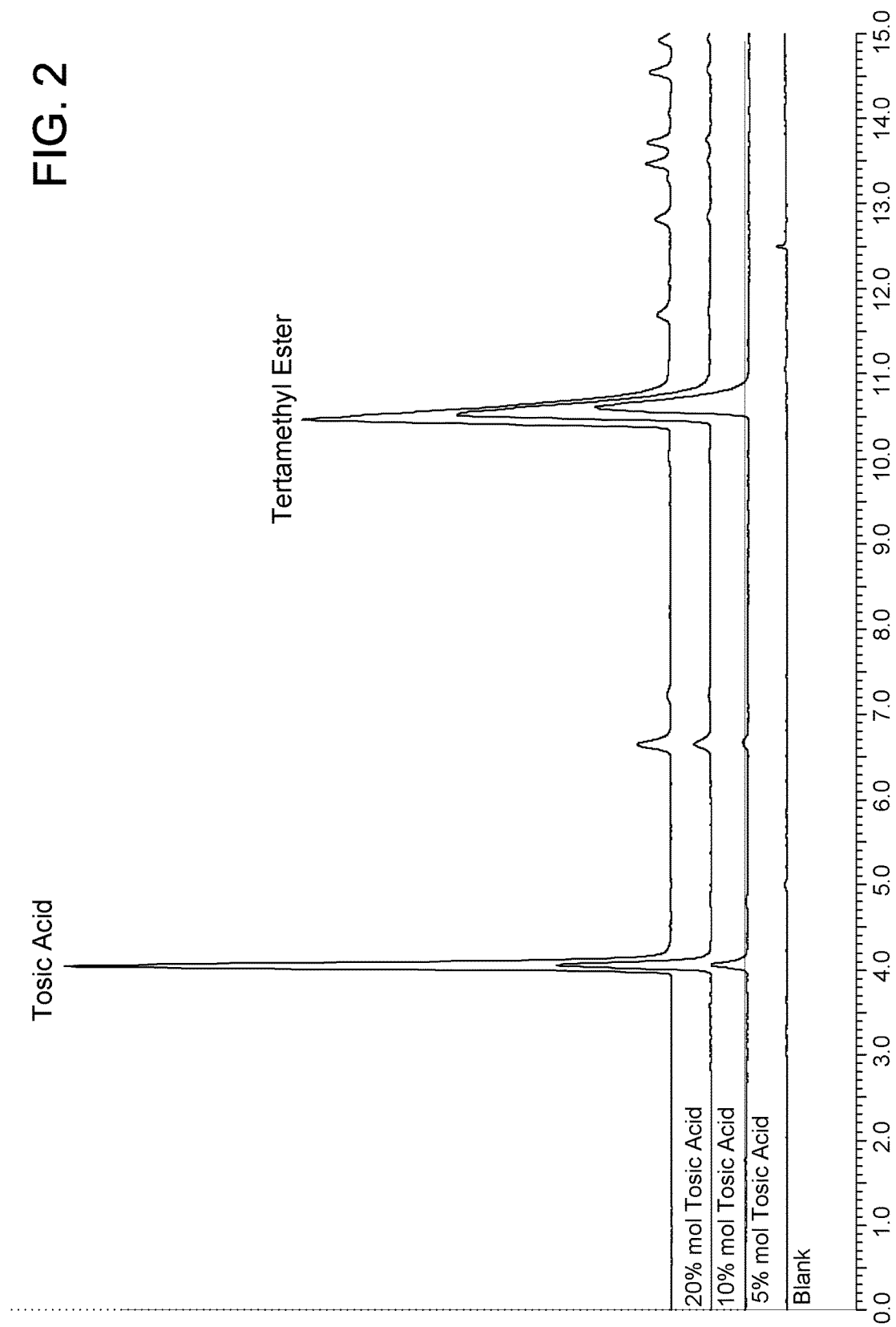
FIG. 2 is a HPLC-ELSD chromatogram for DOTA-tetra (methyl ester) prepared by a process of the present disclosure, and in particular as detailed in Example 1.

The vials were stirred at ambient temperature for 16 hours (overnight). The reaction product was analyzed by HPLC-ELSD using a HILIC column and 85% acetonitrile (0.05% TFA)/10% water (0.05% TFA). The chromatogram is shown in FIG. 2, indicating that 5 mol % and 10 mol % p-toluene sulfonic acid gave approximately 98% of the desired tetramer after correcting for p-toluene sulfonic acid. Additionally, a 20 mol % p-toluene sulfonic acid yielded a tetramer having a higher impurity content.

Example 2: Direct Formation of DOTA Tetra(methyl ester)

Figure 3:
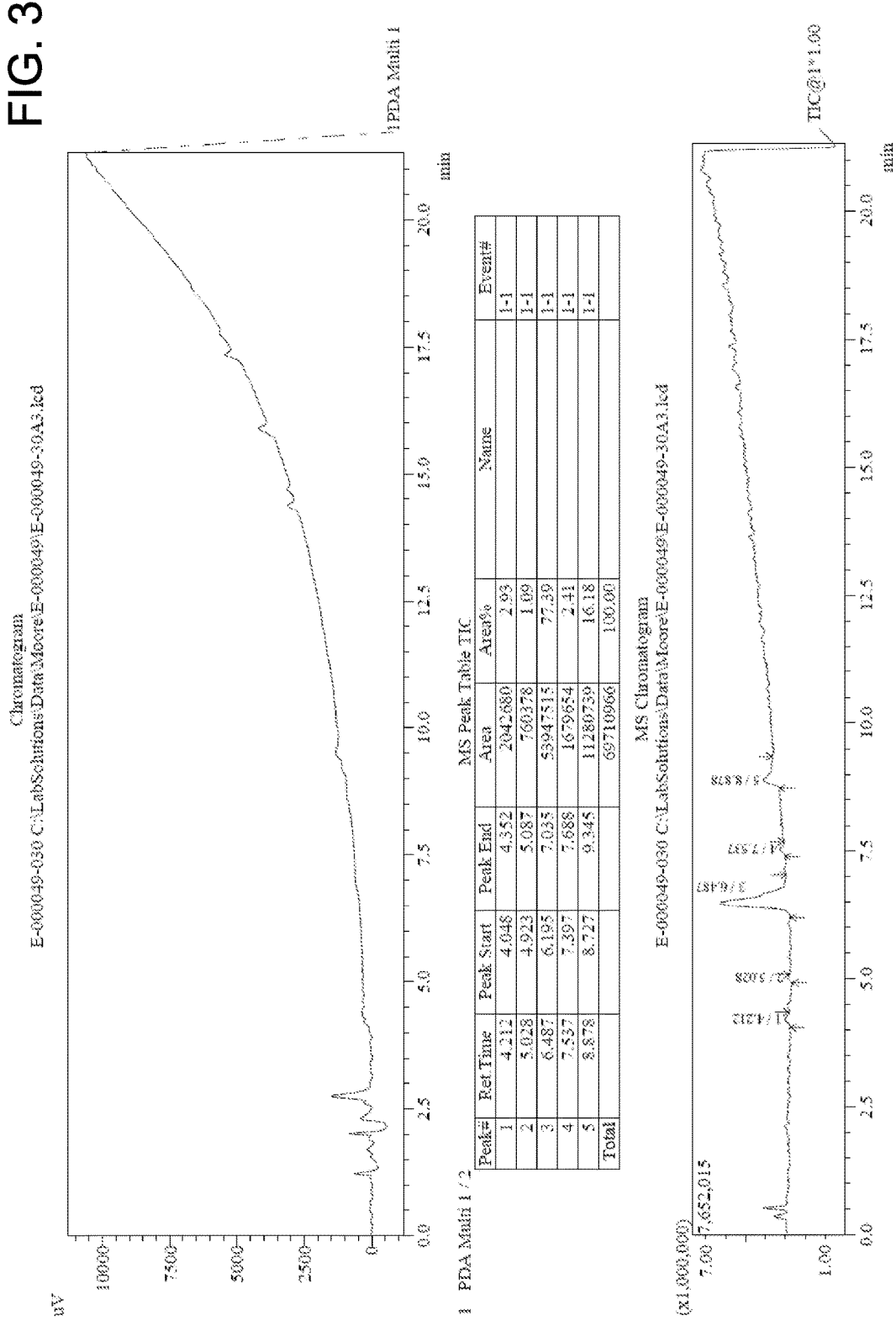
FIG. 3 is a HPLC-MS chromatogram for DOTA-tetra (methyl ester) prepared by a process of the present disclosure, and in particular as detailed in Example 2.

In a 250 mL round-bottom flask methyl 2-(aziridin-1-yl)acetate (8.69 mmol) and 4-methylbenzene sulfonic acid (0.261 mmol) were combined with 50 mL methanol to give a colorless solution. The solution was refluxed under argon overnight to yield 80% yield of DOTA tetra(methyl ester). The reacted solution was analyzed by HPLC MS. The chromatogram is shown in FIG. 3, indicating that 77.4% purity of the desired tetramer was achieved.

Example 3: Survey of Acid/Solvent Combinations for the Cyclotetramerization of Methyl 2-(aziridin-1-yl)acetate A series of reactions were carried out based upon a matrix of reaction conditions consisting of four different acids (trifluoroacetic acid, p-toluene sulfonic acid, hydrochloric acid and sulfuric acid) at three different levels (2, 5, 7 mole %), four different solvents (DMAc, DMF, ACN, and MeOH) at three different concentrations of methyl 2-(azridin-1-yl)acetate (5, 10, 20 uL/mL, which correspond to aziridine concentrations of 0.0414, 0.0828 and 0.166 mmol/mL, respectively). The reactions were analyzed for completeness by HPLC-ELSD using a 90-80 ACN(0.05% TFA)-Water (0.05%) gradient over 15 minutes. The results were quantified by comparing to known concentrations of DOTA-tetramethyl ester, prepared by an independent method. The results are reported in Table 2 below, wherein DMAc refers to dimethylacetamide, DMF refers to dimethylformamide, MeOH refers to methyl alcohol, ACN refers to acetonitrile, TsOH refers to p-toluene sulfonic acid, and TFA refers to trifluoroacetic acid.

TABLE 2

| Run | Solvent | Acid | Mole % Acid | Aziridine Conc. (mmol/mL) | % Yield |
|---|---|---|---|---|---|
| 1 | DMAc | TFA | 2 | 0.0414 | 0 |
| 2 | DMAc | TFA | 2 | 0.0828 | 31 |
| 3 | DMAc | TFA | 2 | 0.166 | 37 |
| 4 | DMAc | TFA | 5 | 0.0414 | 39 |
| 5 | DMAc | TFA | 5 | 0.0828 | 45 |
| 6 | DMAc | TFA | 5 | 0.166 | 68 |
| 7 | DMAc | TFA | 7 | 0.0414 | 58 |
| 8 | DMAc | TFA | 7 | 0.0828 | 45 |
| 9 | DMAc | TFA | 7 | 0.166 | 61 |
| 10 | DMAc | TsOH*H$_2$O | 2 | 0.0414 | 28 |
| 11 | DMAc | TsOH*H$_2$O | 2 | 0.0828 | 37 |
| 12 | DMAc | TsOH*H$_2$O | 2 | 0.166 | 46 |
| 13 | DMAc | TsOH*H$_2$O | 5 | 0.0414 | 59 |
| 14 | DMAc | TsOH*H$_2$O | 5 | 0.0828 | 76 |
| 15 | DMAc | TsOH*H$_2$O | 5 | 0.166 | 74 |
| 16 | DMAc | TsOH*H$_2$O | 7 | 0.0414 | 63 |
| 17 | DMAc | TsOH*H$_2$O | 7 | 0.0828 | 92 |
| 18 | DMAc | TsOH*H$_2$O | 7 | 0.166 | 84 |
| 19 | DMAc | H$_2$SO$_4$ | 2 | 0.0414 | 0 |
| 20 | DMAc | H$_2$SO$_4$ | 2 | 0.0828 | 40 |
| 21 | DMAc | H$_2$SO$_4$ | 2 | 0.166 | 51 |
| 22 | DMAc | H$_2$SO$_4$ | 5 | 0.0414 | 58 |
| 23 | DMAc | H$_2$SO$_4$ | 5 | 0.0828 | 76 |
| 24 | DMAc | H$_2$SO$_4$ | 5 | 0.166 | 58 |
| 25 | DMAc | H$_2$SO$_4$ | 7 | 0.0414 | 20 |
| 26 | DMAc | H$_2$SO$_4$ | 7 | 0.0828 | 81 |
| 27 | DMAc | H$_2$SO$_4$ | 7 | 0.166 | 0 |
| 28 | DMAc | HCl (aq) | 2 | 0.0414 | 7 |
| 29 | DMAc | HCl (aq) | 2 | 0.0828 | 0 |
| 30 | DMAc | HCl (aq) | 2 | 0.166 | 2 |
| 31 | DMAc | HCl (aq) | 5 | 0.0414 | 0 |
| 32 | DMAc | HCl (aq) | 5 | 0.0828 | 4 |
| 33 | DMAc | HCl (aq) | 5 | 0.166 | 2 |
| 34 | DMAc | HCl (aq) | 7 | 0.0414 | 8 |
| 35 | DMAc | HCl (aq) | 7 | 0.0828 | 4 |
| 36 | DMAc | HCl (aq) | 7 | 0.166 | 2 |
| 37 | DMF | TFA | 2 | 0.0414 | 0 |
| 38 | DMF | TFA | 2 | 0.0828 | 32 |
| 39 | DMF | TFA | 2 | 0.166 | 42 |
| 40 | DMF | TFA | 5 | 0.0414 | 43 |
| 41 | DMF | TFA | 5 | 0.0828 | 38 |
| 42 | DMF | TFA | 5 | 0.166 | 61 |
| 43 | DMF | TFA | 7 | 0.0414 | 52 |
| 44 | DMF | TFA | 7 | 0.0828 | 68 |
| 45 | DMF | TFA | 7 | 0.166 | 68 |
| 46 | DMF | TsOH*H$_2$O | 2 | 0.0414 | 22 |
| 47 | DMF | TsOH*H$_2$O | 2 | 0.0828 | 30 |
| 48 | DMF | TsOH*H$_2$O | 2 | 0.166 | 43 |
| 49 | DMF | TsOH*H$_2$O | 5 | 0.0414 | 47 |
| 50 | DMF | TsOH*H$_2$O | 5 | 0.0828 | 54 |
| 51 | DMF | TsOH*H$_2$O | 5 | 0.166 | 67 |
| 52 | DMF | TsOH*H$_2$O | 7 | 0.0414 | 58 |
| 53 | DMF | TsOH*H$_2$O | 7 | 0.0828 | 74 |
| 54 | DMF | TsOH*H$_2$O | 7 | 0.166 | 74 |
| 55 | DMF | H$_2$SO$_4$ | 2 | 0.0414 | 23 |
| 56 | DMF | H$_2$SO$_4$ | 2 | 0.0828 | 37 |
| 57 | DMF | H$_2$SO$_4$ | 2 | 0.166 | 35 |
| 58 | DMF | H$_2$SO$_4$ | 5 | 0.0414 | 60 |
| 59 | DMF | H$_2$SO$_4$ | 5 | 0.0828 | 66 |
| 60 | DMF | H$_2$SO$_4$ | 5 | 0.166 | 16 |
| 61 | DMF | H$_2$SO$_4$ | 7 | 0.0414 | 59 |
| 62 | DMF | H$_2$SO$_4$ | 7 | 0.0828 | 4 |
| 63 | DMF | H$_2$SO$_4$ | 7 | 0.166 | 59 |
| 64 | DMF | HCl (aq) | 2 | 0.0414 | 7 |
| 65 | DMF | HCl (aq) | 2 | 0.0828 | 4 |
| 66 | DMF | HCl (aq) | 2 | 0.166 | 3 |
| 67 | DMF | HCl (aq) | 5 | 0.0414 | 8 |
| 68 | DMF | HCl (aq) | 5 | 0.0828 | 4 |
| 69 | DMF | HCl (aq) | 5 | 0.166 | 3 |
| 70 | DMF | HCl (aq) | 7 | 0.0414 | 8 |
| 71 | DMF | HCl (aq) | 7 | 0.0828 | 5 |
| 72 | DMF | HCl (aq) | 7 | 0.166 | 4 |
| 73 | MeOH | TFA | 2 | 0.0414 | 13 |
| 74 | MeOH | TFA | 2 | 0.0828 | 15 |
| 75 | MeOH | TFA | 2 | 0.166 | 17 |
| 76 | MeOH | TFA | 5 | 0.0414 | 38 |
| 77 | MeOH | TFA | 5 | 0.0828 | 41 |
| 78 | MeOH | TFA | 5 | 0.166 | 38 |
| 79 | MeOH | TFA | 7 | 0.0414 | 56 |
| 80 | MeOH | TFA | 7 | 0.0828 | 62 |
| 81 | MeOH | TFA | 7 | 0.166 | 57 |
| 82 | MeOH | TsOH*H$_2$O | 2 | 0.0414 | 16 |
| 83 | MeOH | TsOH*H$_2$O | 2 | 0.0828 | 18 |
| 84 | MeOH | TsOH*H$_2$O | 2 | 0.166 | 19 |
| 85 | MeOH | TsOH*H$_2$O | 5 | 0.0414 | 31 |
| 86 | MeOH | TsOH*H$_2$O | 5 | 0.0828 | 40 |
| 87 | MeOH | TsOH*H$_2$O | 5 | 0.166 | 39 |

TABLE 2-continued

| Run | Solvent | Acid | Mole % Acid | Aziridine Conc. (mmol/mL) | % Yield |
|---|---|---|---|---|---|
| 88 | MeOH | TsOH*H$_2$O | 7 | 0.0414 | 43 |
| 89 | MeOH | TsOH*H$_2$O | 7 | 0.0828 | 57 |
| 90 | MeOH | TsOH*H$_2$O | 7 | 0.166 | 52 |
| 91 | MeOH | H$_2$SO$_4$ | 2 | 0.0414 | 17 |
| 92 | MeOH | H$_2$SO$_4$ | 2 | 0.0828 | 23 |
| 93 | MeOH | H$_2$SO$_4$ | 2 | 0.166 | 26 |
| 94 | MeOH | H$_2$SO$_4$ | 5 | 0.0414 | 36 |
| 95 | MeOH | H$_2$SO$_4$ | 5 | 0.0828 | 42 |
| 96 | MeOH | H$_2$SO$_4$ | 5 | 0.166 | 44 |
| 97 | MeOH | H$_2$SO$_4$ | 7 | 0.0414 | 34 |
| 98 | MeOH | H$_2$SO$_4$ | 7 | 0.0828 | 48 |
| 99 | MeOH | H$_2$SO$_4$ | 7 | 0.166 | 40 |
| 100 | MeOH | HCl (aq) | 2 | 0.0414 | 14 |
| 101 | MeOH | HCl (aq) | 2 | 0.0828 | 16 |
| 102 | MeOH | HCl (aq) | 2 | 0.166 | 12 |
| 103 | MeOH | HCl (aq) | 5 | 0.0414 | 31 |
| 104 | MeOH | HCl (aq) | 5 | 0.0828 | 37 |
| 105 | MeOH | HCl (aq) | 5 | 0.166 | 28 |
| 106 | MeOH | HCl (aq) | 7 | 0.0414 | 43 |
| 107 | MeOH | HCl (aq) | 7 | 0.0828 | 49 |
| 108 | MeOH | HCl (aq) | 7 | 0.166 | 40 |
| 109 | ACN | TFA | 2 | 0.0414 | 18 |
| 110 | ACN | TFA | 2 | 0.0828 | 22 |
| 111 | ACN | TFA | 2 | 0.166 | 28 |
| 112 | ACN | TFA | 5 | 0.0414 | 28 |
| 113 | ACN | TFA | 5 | 0.0828 | 44 |
| 114 | ACN | TFA | 5 | 0.166 | 49 |
| 115 | ACN | TFA | 7 | 0.0414 | 40 |
| 116 | ACN | TFA | 7 | 0.0828 | 56 |
| 117 | ACN | TFA | 7 | 0.166 | 64 |
| 118 | ACN | TsOH*H$_2$O | 2 | 0.0414 | 18 |
| 119 | ACN | TsOH*H$_2$O | 2 | 0.0828 | 24 |
| 120 | ACN | TsOH*H$_2$O | 2 | 0.166 | 26 |
| 121 | ACN | TsOH*H$_2$O | 5 | 0.0414 | 38 |
| 122 | ACN | TsOH*H$_2$O | 5 | 0.0828 | 52 |
| 123 | ACN | TsOH*H$_2$O | 5 | 0.166 | 55 |
| 124 | ACN | TsOH*H$_2$O | 7 | 0.0414 | 52 |
| 125 | ACN | TsOH*H$_2$O | 7 | 0.0828 | 60 |
| 126 | ACN | TsOH*H$_2$O | 7 | 0.166 | 66 |
| 127 | ACN | H$_2$SO$_4$ | 2 | 0.0414 | 0 |
| 128 | ACN | H$_2$SO$_4$ | 2 | 0.0828 | 21 |
| 129 | ACN | H$_2$SO$_4$ | 2 | 0.166 | 2 |
| 130 | ACN | H$_2$SO$_4$ | 5 | 0.0414 | 32 |
| 131 | ACN | H$_2$SO$_4$ | 5 | 0.0828 | 50 |
| 132 | ACN | H$_2$SO$_4$ | 5 | 0.166 | 2 |
| 133 | ACN | H$_2$SO$_4$ | 7 | 0.0414 | 48 |
| 134 | ACN | H$_2$SO$_4$ | 7 | 0.0828 | 59 |
| 135 | ACN | H$_2$SO$_4$ | 7 | 0.166 | 2 |
| 156 | ACN | HCl (aq) | 2 | 0.0414 | 7 |
| 137 | ACN | HCl (aq) | 2 | 0.0828 | 4 |
| 138 | ACN | HCl (aq) | 2 | 0.166 | 32 |
| 139 | ACN | HCl (aq) | 5 | 0.0414 | 8 |
| 140 | ACN | HCl (aq) | 5 | 0.0828 | 32 |
| 141 | ACN | HCl (aq) | 5 | 0.166 | 56 |
| 142 | ACN | HCl (aq) | 7 | 0.0414 | 8 |
| 143 | ACN | HCl (aq) | 7 | 0.0828 | 6 |
| 144 | ACN | HCl (aq) | 7 | 0.166 | 63 |

The best yields of DOTA tetra(methyl ester) were achieved with DMAc and p-toluene sulfonic acid, with 92% and 84% in two independent runs.

Example 4: Preparation of Gd-DOTA Chelate of Formula (IIIa) Wherein $R^1$ and $R^2$ are Hydrogen; $X^1$ is —OH; and $M^{n+}$ is $Gd^{3+}$ A mixture of sodium 2-aziridinylacetate (40 mmol) and gadolinium chloride or gadolinium acetate (10 mmol) in water (50 mL) may be stirred at ambient temperature for 16 hours (overnight). After the reaction, the solution may have the pH adjusted to about 7 by means of the addition of 10 mmol N-methyl glucamine (meglumine) The solvent may be removed in vacuo and the crude material may be purified by crystallization, or the reaction mixture may be purified chromatography, or the mixture may be purified by nano-filtration and the resulting solution spray dried to give the meglumine salt of gadoteric acid.

When introducing elements of the present disclosure or the embodiment(s) thereof, the articles "a", "an", "the" and "said" are intended to mean that there are one or more of the elements. The terms "comprising", "including" and "having" are intended to be inclusive and mean that there may be additional elements other than the listed elements.

In view of the above, it will be seen that the several feature or objects of the disclosure are achieved and other advantageous results attained.

As various changes could be made in the above compositions, products, and methods (including concentrations of reagents, process conditions, etc.) without departing from the scope of the present disclosure, it is intended that all matter contained in the above description shall be interpreted as illustrative and not in a limiting sense.

What is claimed is:

1. A process for the preparation of 1,4,7,10-tetraaza-1,4,7,10-tetrakis(carboxymethyl)cyclododecane (DOTA), the process comprising:
   (i) forming a reaction mixture comprising (a) a stoichiometric amount of an aziridine of Formula (Ib), (b) a Brønsted acid, and (c) a solvent; and,
   (ii) reacting the contents of the reaction mixture to form DOTA by cyclotetramerization of the aziridine of Formula (Ib), according to the following reaction:

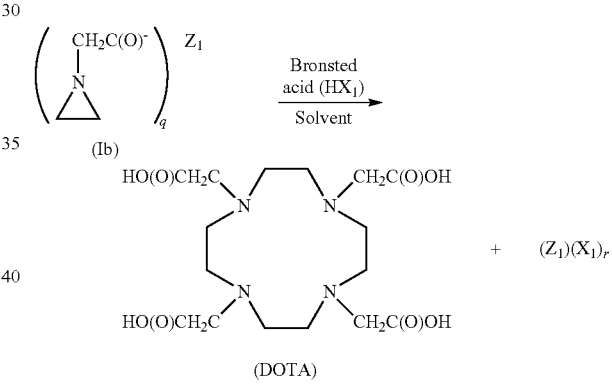

wherein:
   HX$_1$ is a Brønsted acid;
   Z$_1$ is an alkali metal having a +1 charge or an alkaline earth metal having a +2 charge; and
   q and rare 1 when Z$_1$ is an alkali metal and q and rare 2 when Z$_1$ is an alkaline earth metal.

2. The process of claim 1 wherein the Brønsted acid is selected from the group consisting of p-toluenesulfonic acid, methane sulfonic acid, triflic acid, sulfuric acid, hydrochloric acid, hydroiodic acid, hydrobromic acid, hydrofluoric acid, phosphoric acid, perchloric acid, trifluoroacetic acid, triethylammonium chloride, triethylammonium bromide, triethylammonium acetate, triethylammonium formate, tris(2-hydroxyethyl)ammonium chloride, tris(2-hydroxyethyl)ammonium bromide, tris(2-hydroxyethyl)ammonium acetate, tris(2-hydroxyethyl)ammonium formate, 4,7,13,16,21,24-hexaoxa-1,10-diazabicyclo[8.8.8]hexacosan-1-ium chloride, bromide, tris(2-hydroxyethyl)ammonium acetate, 4,7,13,16,21,24-hexaoxa-1,10-diazabicyclo[8.8.8]hexacosan-1-ium formate, bis(isopropyl)ethylammonium chloride, bis(isopropyl)ethylammonium bromide, bis(isopropyl)ethylammonium acetate, bis(isopropyl)ethylammonium formate, tris(carboxymethyl)ammonium chloride, tris(carboxymethyl)ammonium bromide, tris(carboxymethyl)ammonium acetate, tris(carboxymethyl)ammonium formate, 2-(bis(carboxymethyl)amino)-N,N-bis(carboxymethyl)ethanaminium chloride, 2-(bis(carboxymethyl)amino)-N,N-bis(carboxymethyl)ethanaminium bromide, 2-(bis(carboxymethyl)amino)-N,N-bis(carboxymethyl)ethanaminium acetate, bis 2-(bis(carboxymethyl)amino)-N,N-bis(carboxymethyl)ethanaminium formate, 2-(bis(carboxymethyl)amino)-N-(2-(bis(carboxymethyl)amino)ethyl)-N-(carboxymethyl)ethanaminium, 2-(bis(carboxymethyl)amino)-N-(2-(bis(carboxymethyl)amino)ethyl)-N-(carboxymethyl)ethanaminium bromide, 2-(bis(carboxymethyl)amino)-N-(2-(bis(carboxymethyl)amino)ethyl)-N-(carboxymethyl)ethanaminium acetate, 2-(bis(carboxymethyl)amino)-N-(2-(bis(carboxymethyl)amino)ethyl)-N-(carboxymethyl)ethanaminium formate, formic acid, acetic acid, succinic acid, benzoic acid, lactic acid, citric acid, oxalic acid, nitriloacetic acid, ethylenediaminetetraacetic acid, diethylenetriaminepentacetic acid and combinations thereof.

3. The process of claim 1 wherein the Brønsted acid is selected from the group consisting of p-toluenesulfonic acid, trifluoroacetic acid, hydrochloric acid and sulfuric acid.

4. The process of claim 1 wherein $Z_1$ is $Na^+$, $K^+$, $Ca^{2+}$ or $Mg^{2+}$ and $X_1$ is $Br^-$, $Cl^-$ or $OSO_3^{2-}$.

5. The process of claim 1 wherein the amount of the Brønsted acid, expressed as the ratio of equivalents of the acid to equivalents of aziridine, is from about 0.01:1 to about 0.5:1, from about 0.03:1 to about 0.1:1, or from about 0.04:1 to about 0.08:1.

6. The process of claim 1 further comprising treating DOTA with a metal cation, $M^{n+}$, wherein n+ is 2 or 3, provided from a metal ion source selected from the group consisting of metal oxides, metal carbonates, and weak chelates to form a metal-DOTA chelate of Formula (IIb) or Formula (IIc):

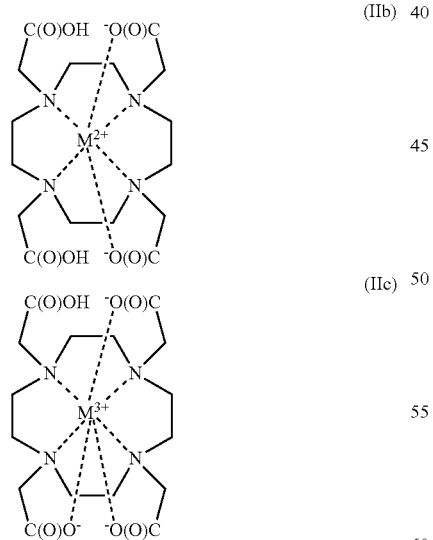

wherein the metal cation is selected from the group consisting of Gd, Eu, Tb, Dy, Sm, Lu, La, In, Ga, Re, Ru, Fe, Cu, Zn, Ni, Co, Cr, V, Ti Sc, Zr, Nb, Mo, Rh, Pd, Ag, Cd, Sn, Hf, Ta, W, Os, Ir, Pt, Au and Y, and wherein $M^{2+}$ coordination can occur with any two of the carboxyl moieties.

7. The process of claim 6 wherein the metal ion source is a chelate of acetylacetonate or $Gd_2O_3$ and compound Formula (IIc) is gadoteric acid.

8. The process of claim 1 wherein the solvent comprises water.

9. The process of claim 8 wherein the solvent consists essentially of water.

10. The process of claim 1 wherein aziridine Formula (Ib) is prepared according to the following reaction scheme:

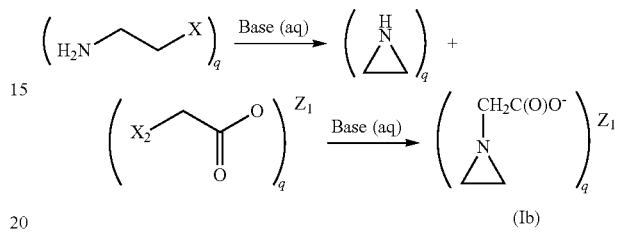

wherein X is a leaving group, $X_2$ is a halide, $Z_1$ is an alkali metal having a +1 charge or an alkaline earth metal having a +2 charge, q is 1 when $Z_1$ has a +1 charge, and q is 2 when $Z_1$ has a +2 charge.

11. The process of claim 10 wherein X is Cl, Br or $OSO_3^-$, the base is NaOH or KOH and $Z_1$ is $Na^+$, $K^+$, $Ca^{2+}$ or $Mg^{2+}$.

12. The process of claim 1 wherein the reaction temperature is from about −20° C. to about 150° C., from about 0° C. to about 100° C., from about 10° C. to about 50° C., or from about 20° C. to about 30° C.

13. The process of claim 1 wherein the concentration of the aziridine in the reaction mixture is from about 0.05 to about 1.0 equivalents per liter, from about 0.1 to about 0.5 equivalents per liter, or from about 0.1 to about 0.3 equivalents per liter.

14. The process of claim 6 further comprising purifying reaction product Formula (IIb), Formula (IIc), or gadoteric acid and isolating reaction product Formula (IIb), Formula (IIc), or gadoteric acid, wherein
(i) the purity of the compound Formula (IIb), Formula (IIc), or gadoteric acid is at least about 50%, at least about 60%, at least about 70%, at least about 80%, or at least about 90% as measured by MS chromatogram, or
(ii) the molar yield of the compound Formula (IIb), Formula (IIc), or gadoteric acid is at least about 40%, at least about 50%, at least about 60%, at least about 70%, at least about 80%, or at least about 90% based on equivalents of aziridine.

15. The process of claim 14 wherein purification is by nanofiltration.

16. The process of claim 15 wherein the gadoteric acid is nanofiltered as the meglumine salt thereof.

17. The process of claim 15 wherein the DOTA is nanofiltered as the sodium salt thereof.

18. The process of claim 14 wherein isolation is by crystallization from aqueous solvent at a pH of from about 1 to about 4.

19. The process of claim 18 wherein the reaction product is gadoteric acid and the crystallization pH is from about 2 to about 4.

20. The process of claim 1 further comprising purifying reaction product DOTA and isolating reaction product Formula (IIb), Formula (IIc), DOTA or gadoteric acid, wherein (i) the purity of the compound DOTA is at least about 50%, at least about 60%, at least about 70%, at least about 80%, or at least about 90% as measured by MS chromatogram, or (ii) the molar yield of the compound DOTA is at least about 40%, at least about 50%, at least about 60%, at least about 70%, at least about 80%, or at least about 90% based on equivalents of aziridine.

21. A process for the preparation of a macrocyclic tetramer compound of Formula (IIe), the process comprising:

(i) forming a reaction mixture comprising (a) a stoichiometric amount of an aziridine of Formula (Ib), (b) a Lewis acid, and (c) a solvent; and, (ii) reacting the contents of the reaction mixture to form a metal-1,4,7,10-tetraaza-1,4,7,10-tetrakis(carboxymethyl)cyclododecane (DOTA) chelate of Formula (IIe) by cyclotetramerization of the aziridine of Formula (Ib), according to the following reaction:

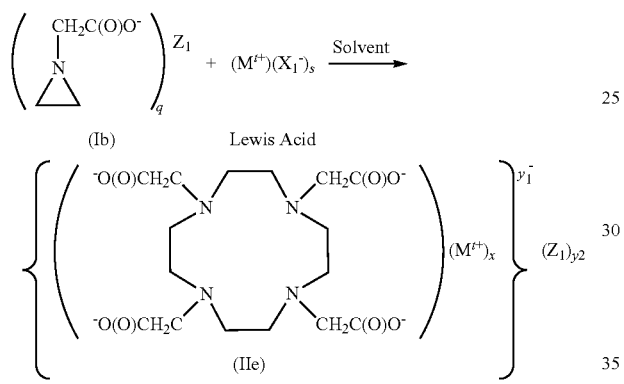

wherein:

$(M^{t+})(X_1^-)_s$ is a chelatable Lewis acid metal salt formed from a cation, M, and an anion, $X_1^-$, wherein t is 1, 2 or 3 and s is selected to achieve electrical neutrality;

$Z_1$ is hydrogen, an alkali metal having a +1 charge or an alkaline earth metal having a +2 charge;

q is 1 when $Z_1$ is an alkali metal and q is 2 when $Z_1$ is an alkaline earth metal; and t is 3 and x is 1, or t is 2 and x is 1, or t is 2 and x is 2, or t is 1 and x is 1, or t is 1 and x is 2, or t is 1 and x is 3 or t is 1 and x is 4, wherein:

(a) $y_1=y_2=(4-(X*t))$ when $Z_1$ has a +1 charge, and (b) $y_1=(4-(X*t))$ and $y_2=(y_1/2)$ when $Z_1$ has a +2 charge according to the following table

| | | $Z_1$ = +1 | $Z_2$ = +2 | |
|---|---|---|---|---|
| t | X | $y_1$ and $y_2$ | $y_1$ | $y_2$ |
| 3 | 1 | 1 | 1 | ½ |
| 2 | 1 | 2 | 2 | 1 |
| 2 | 2 | 0 | 0 | 0 |
| 1 | 1 | 3 | 3 | 3/2 |
| 1 | 2 | 2 | 2 | 1 |
| 1 | 3 | 1 | 1 | ½ |
| 1 | 4 | 0 | 0 | 0. |

22. The process of claim 21 wherein the Lewis acid is selected from the group consisting of boron tribromide, boron trichloride, boron trifluoride, boron trifluoride etherate, gadolinium tribromide, gadolinium trichloride, gadolinium trifluoride, gadolinium acetate, gadolinium formate, cupric bromide, cupric chloride, cupric fluoride, nickel bromide, nickel chloride, nickel fluoride aluminum bromide, aluminum chloride, aluminum fluoride, ferric bromide, ferric chloride, ferric fluoride, sodium bromide, potassium bromide, potassium chloride, potassium fluoride, sodium chloride, sodium fluoride, tin(IV) chloride, and combinations thereof.

23. The process of claim 21 wherein the amount of the Lewis acid, expressed as the ratio of equivalents of the acid to equivalents of aziridine compound, is from about 0.05:1 to about 1.5:1, from about 0.05:1 to about 1.2:1, or from about 0.5:1 to about 1.2:1.

24. The process of claim 21 wherein the ratio of Lewis acid, expressed as the ratio of equivalents of the acid to equivalents of aziridine compound, is from about 0.05:1 to about 0.5:1 or from about 0.1:1 to about 0.5:1.

25. The process of claim 21 wherein the ratio Lewis acid, expressed as the ratio of equivalents of the acid to equivalents of aziridine compound, is from about 1.0:1 to about 1.5:1 or from about 1.0:1 to about 1.2:1.

26. The process of claim 21 wherein Formula (IIe) is of Formula (IIf):

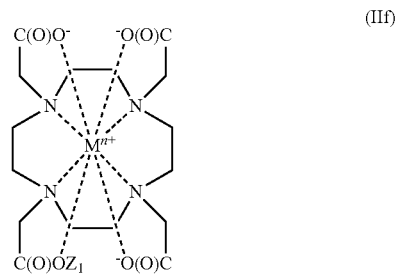

wherein n is 3 and $Z_1$ is hydrogen or an alkali metal having a +1 charge.

27. The process of claim 26 wherein Formula (IIf) is gadoteric acid wherein $M^{n+}$ is $Gd^{3+}$ and $Z_1$ is hydrogen.

28. The process of any claim 21 wherein the solvent comprises water.

29. The process of claim 28 wherein the solvent consists essentially of water.

30. The process of claim 21 wherein aziridine Formula (Ib) is prepared according to the following reaction scheme:

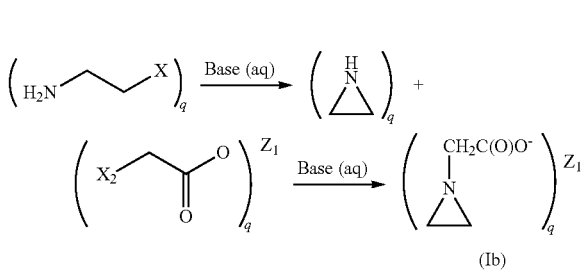

wherein X is a leaving group, $X_2$ is a halide, $Z_1$ is an alkali metal having a +1 charge or an alkaline earth metal having a +2 charge, q is 1 when $Z_1$ has a +1 charge, and q is 2 when $Z_1$ has a +2 charge.

31. The process of claim 30 wherein X is Cl, Br or $OSO_3^-$, the base is NaOH or KOH and $Z_1$ is $Na^+$, $K^+$, $Ca^{2+}$ or $Mg^{2+}$.

32. The process of claim 21 wherein the reaction temperature is from about −20° C. to about 150° C., from about 0° C. to about 100° C., from about 10° C. to about 50° C., or from about 20° C. to about 30° C.

33. The process of claim 21 wherein the concentration of the aziridine in the reaction mixture is from about 0.05 to about 1.0 equivalents per liter, from about 0.1 to about 0.5 equivalents per liter, or from about 0.1 to about 0.3 equivalents per liter.

34. The process of claim 21 further comprising purifying and isolating reaction product Formula (IIe), wherein:
  (i) the purity of the compound Formula (IIe) is at least about 50%, at least about 60%, at least about 70%, at least about 80%, or at least about 90% as measured by MS chromatogram, or
  (ii) the molar yield of the compound Formula (IIe) is at least about 40%, at least about 50%, at least about 60%, at least about 70%, at least about 80%, or at least about 90% based on equivalents of aziridine.

35. The process of claim 34 wherein purification is by nanofiltration.

36. The process of claim 35 wherein the gadoteric acid is nanofiltered as the meglumine salt thereof.

37. The process of claim 35 wherein the DOTA is nanofiltered as the sodium salt thereof.

38. The process of claim 34 wherein isolation is by crystallization from aqueous solvent at a pH of from about 1 to about 4.

39. The process of claim 38 wherein the reaction product is gadoteric acid and the crystallization pH is from about 2 to about 4.

* * * * *